US008535681B2

(12) United States Patent
Farinas et al.

(10) Patent No.: US 8,535,681 B2
(45) Date of Patent: Sep. 17, 2013

(54) SUSTAINED DRUG DELIVERY SYSTEM

(76) Inventors: Kathleen Cogan Farinas, Los Altos, CA (US); Steven Chamow, San Mateo, CA (US)

( * ) Notice: Subject to any disclaimer, the term of this patent is extended or adjusted under 35 U.S.C. 154(b) by 0 days.

(21) Appl. No.: 13/124,654

(22) PCT Filed: Oct. 15, 2009

(86) PCT No.: PCT/US2009/060918
§ 371 (c)(1),
(2), (4) Date: Apr. 15, 2011

(87) PCT Pub. No.: WO2010/045506
PCT Pub. Date: Apr. 22, 2010

(65) Prior Publication Data
US 2011/0200599 A1 Aug. 18, 2011

Related U.S. Application Data

(60) Provisional application No. 61/106,136, filed on Oct. 16, 2008.

(51) Int. Cl.
*A61K 39/00* (2006.01)
*A61K 39/44* (2006.01)
*A61K 39/395* (2006.01)
*A61K 38/10* (2006.01)
*A61K 38/08* (2006.01)
*C07K 19/00* (2006.01)
*C07K 16/22* (2006.01)
*C07K 4/12* (2006.01)
*C07K 14/00* (2006.01)

(52) U.S. Cl.
USPC .................. 424/192.1; 424/193.1; 424/185.1; 424/134.1; 424/145.1

(58) Field of Classification Search
None
See application file for complete search history.

(56) References Cited

U.S. PATENT DOCUMENTS

| | | | | |
|---|---|---|---|---|
| 3,979,508 | A * | 9/1976 | Stahmann et al. | 424/9.81 |
| 5,965,371 | A * | 10/1999 | Marasco et al. | 435/7.1 |
| 6,150,461 | A * | 11/2000 | Takei et al. | 525/63 |
| 7,125,542 | B2 * | 10/2006 | Miller et al. | 424/9.61 |
| 7,244,438 | B2 | 7/2007 | Lingnau et al. | |
| 7,259,140 | B2 * | 8/2007 | San Antonio et al. | 514/21.3 |
| 7,316,811 | B2 | 1/2008 | Zhao et al. | |
| 2002/0173456 | A1 * | 11/2002 | Smith et al. | 514/12 |
| 2003/0171320 | A1 * | 9/2003 | Guyer | 514/44 |
| 2004/0037834 | A1 * | 2/2004 | Woloski et al. | 424/178.1 |
| 2005/0260153 | A1 * | 11/2005 | Calias et al. | 424/78.27 |
| 2007/0258975 | A1 | 11/2007 | Hagewiesche et al. | |

OTHER PUBLICATIONS

Yu et al, Investigative Ophthalmology & Visual Science 49(2): 522-527, Feb. 2008.*
Stancovski et al, Proceedings of the National Academy of Science USA 88: 8691-8695, 1991.*
Riemer et al, Mol. Immunol. 42: 1121-1124, 2005.*
http://en.Wikipedia.org/wili/amino_acid, download on Aug. 23, 2012.*
Chirila T.V. and Y. Hong, The Vitreous Humor, in Handbook of Biomaterial Properties, Ed. J. Black and G. Hastings, 1998, Chapman & Hall, pp. 125-131.
Diego A. Gianolio et al., Hyaluronan-Tethered Opioid Depots: Synthetic Stra tegies and Release Kinetics In Vitro and In Vivo, Bioconjugate Chem. Aug. 2008, vol. 19, pp. 1767-1774.
Doronina, S.O. et al. Development of potent monoclonal antibody auristatin conjugates for cancer therapy. Nature Biotechnol. 21: 778-782 (2003).
Ellman G.L. A colorimteric method for determining low concentrations of mercaptans. Arch Biochem Biophys 74: 443-450 (1958).
Gaudreault J. et al. Preclinical pharmacokinetics of Ranibizumab (rhuFabV2) after a single intravitreal administration, Invest. Ophthahnol. Vis. Sci. 46: 726-733 (2005).
Marta Jokiel et al., The Interaction between Polycationic Poly-Lysine Dendr imers and Charged and Neutral Fluorescent Probes, J. Fluoresc. 2007, vol. 1 7, pp. 73-79.
Rosenfeld P. J. Intravitreal Avastin: The low cost alternative to Lucentis?, Am. J. Ophth. 142(1):141-143 (2006).
Singh M. P. et al. Mathematical modeling of drug release from hydrogel matrices via a diffusion coupled with desorption mechanism, J. Cont. Rel., 32, 17-25 (1994).
Singh M.P. et al. Effect of electrostatic interactions on polylysine release rates from collagen matrices and comparison with model predictions, J. Cont. Rel., 35: 165-179 (1995).

* cited by examiner

*Primary Examiner* — Phuong Huynh
(74) *Attorney, Agent, or Firm* — Convergence Intellectual Property Law P.C.; D. Bommi Bommannan; Steven Gong

(57) ABSTRACT

A drug composition comprising a charged moiety coupled to a therapeutic compound is disclosed. The charged moiety is configured to interact with at least one type of component of opposite charge in a biological tissue to create an in situ depot for prolonged drug delivery. The biological tissue may be eye tissue or any tissue containing charged components. Further, a method of treating the human body is disclosed. The method is for introducing into a human body a drug composition comprising a charged moiety coupled to a therapeutic compound. Introduction may be through injection. A method of manufacturing a drug composition comprising a charged moiety coupled to a therapeutic compound is also disclosed.

14 Claims, 12 Drawing Sheets

Figure 1a
Figure 1b
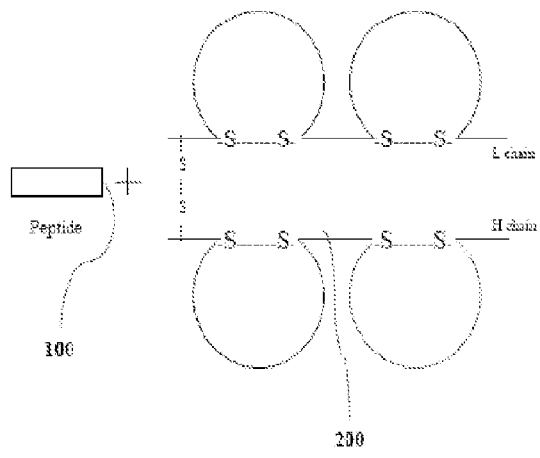
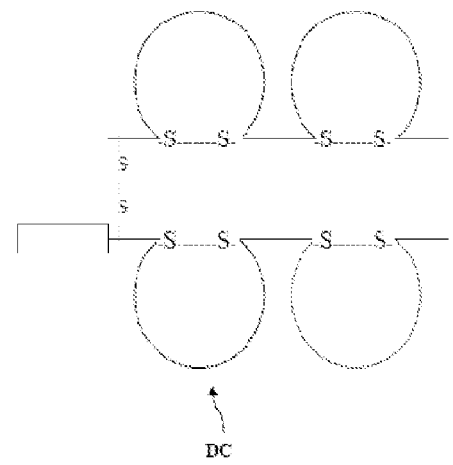

The repeating disaccharide unit of hyaluronan (-4GlcUAβ1-3GlcNAcβ1-)$_n$

L-Lysine          L-Histidine          L-Arginine

Glycine

SUSTAINED DRUG DELIVERY SYSTEM

CROSS-REFERENCE TO RELATED APPLICATIONS

This application claims priority to U.S. Provisional Patent Application No. 61/106,136 filed on Oct. 16, 2008.

FIELD OF THE INVENTION

This invention relates generally to therapeutics and specifically to drug delivery methodologies for prolonging in vivo efficacy of the drug, and more particularly to drug delivery to the back of the eye.

DESCRIPTION OF THE RELATED ART

Diseases of the back of the eye, such as age-related macular degeneration (AMD) and diabetic retinopathy, are affecting increasing numbers of people as our population ages. For efficacious therapy of these degenerative ocular diseases, therapeutic agents need to be delivered at sufficient concentration to the back of the eye, particularly the retina.

Topical delivery of drops is the most common means to administer therapeutic agents to the eye but only a very small percentage of the applied dose reaches the intraocular tissue. Because of the blood-retina-barrier, systemic administration requires large doses to reach therapeutic levels in the eye and therefore may cause unacceptable side effects. Direct injection into the vitreous humor within the globe of the eye is attractive because the barrier to the retina from this site is minimal. However, penetration of the globe can be associated with serious sight-threatening adverse events including infection and retinal detachments. Injections outside of the globe (e.g., subconjunctival) are inefficient in reaching the target tissue due to clearance of the therapeutic agent to the bloodstream in the choroid and the tight barrier of the retinal pigment epithelium to hydrophilic compounds. Some therapeutics in the form of nanoparticles and liposomes can be introduced via intravitreal injections. However, they tend to obscure vision by scattering light entering the eye.

Another method of delivering therapeutic compounds to the eye is the use of implants. For example, two non-biodegradable ophthalmic implants are currently on the market, delivering ganciclovir and fluocinolone acetonide to treat cytomegalovirus retinitis and uveitis, respectively. These can achieve steady delivery of small molecules to the vitreous for years. However, this method involves the risks associated with invasive surgery to implant and remove these devices. As an improvement over non-biodegradable implants, biodegradable implants are in clinical studies that require less invasive procedures, possibly even suture-less office implantation.

It will be desirable to provide drug delivery systems that prolong the availability of the drug to the target tissue, but do not have the limitations associated with frequent dosing or interfering with vision.

Recently, treatment of eye diseases such as AMD has been revolutionized by two developments: (1) the realization that vascular endothelial growth factor (VEGF) is a causative factor in the disease, and (2) approval of an anti-VEGF antibody fragment for treatment of AMD administered via intravitreal injection, Genentech's Ranibizumab (LUCENTIS® hereinafter also referred to as Lucentis). In addition, a full length antibody directed against VEGF such as Genentech's Bevacizumab (AVASTIN®, hereinafter also referred to as Avastin), is frequently injected into the vitreous off-label to treat back of the eye diseases. These new treatment options have had a huge impact because they are the first treatments for AMD that improve vision in many patients, where previous treatments simply delayed vision loss. Ranibizumab and Bevacizumab act by binding to and inactivating VEGF. The duration of effect is determined by drug half-life; in general, a longer half-life provides longer duration and, therefore, less frequent dosing.

Clinical pharmocokinetic data are generally limited to serum due to difficulty in sampling ocular tissue. Elimination of Ranibizumab from the eye has been studied more extensively in monkeys (Gaudreault et al., *Invest. Ophthalmol. Vis. Sci.* 46:726-733, 2005). Ranibizumab was cleared uniformly from all ocular compartments, including the vitreous and retina, with a terminal half-life of approximately 3 days. The serum half-life after intravitreal injection was similar, (approximately 3.5 days) whereas the half-life was approximately 0.5 day after intravenous injection. This suggests the serum concentrations after intravitreal injection are controlled by the elimination rate from the eye. The package insert of Lucentis states that " . . . monthly 500 microgram intravitreal injections of Ranibizumab achieve results superior to less frequent dosing". However, given the attendant risks of intravitreal injections noted above, it is widely recognized that physicians would prefer, and patients would benefit from, less frequent dosing.

Further, though methods of sustained drug delivery using cationic complexes are promising, (e.g., see Singh et al., *J. Cont. Rel.*, 32: 17-25, 1994; Singh et al., *J. Cont. Rel.*, 35: 165-179, 1995), they have yet to be applied to treatment of the localized areas of the body such as the eye. For example, U.S. Pat. No. 7,244,438 by Lingnau et al. discloses a drug formulation where cationic amino acids are physically combined with a therapeutic agent for systemic delivery. A physical combination of this sort will not be as suitable for sustained drug delivery as a chemically combined drug composition. Further, the charge density of the cationic moiety that is disclosed by Lingnau et al. would exhibit both undesirably high antigenicity, as well as an undesirably high toxicity.

Further, polycations such as polyethylenimine and polylysine are traditionally often utilized in nonviral gene delivery systems to protect nucleic acid therapeutics (e.g., DNA and siRNA) from degradation and facilitate uptake into cells. Electrostatic complexation between polycationic polymers or lipids and polyanionic nucleic acids results in formation of complexes known as polyplexes or lipoplexes. The condensed nucleic acids are compact and protected from digestion by nuclease. The complexes tend to precipitate from solution and, when formulated with excess polycation, can lead to small particles with positive charge on the surface that stabilizes the particles and promotes uptake into cells by endocytosis. Others have conjugated Another approach has been to link peptides to proteins to achieve targeted delivery. For example, a deca-aspartate bone-targeting peptide has been linked to a fusion protein to reintroduce a missing enzyme directly to the diseased bone tissue (Enobia Pharma, Montreal, Canada). The use of a charged moiety to form an in situ depot for sustained drug use has not been indicated for use in biological tissues such as the eye.

Moreover, development of controlled release systems for proteins and peptides involve additional protein stability challenges. Loss of integrity and activity can occur through aggregation and denaturation during the stresses of manufacturing, storage on the shelf, or during use. Excipients are generally added to address these issues, typically leading to formulations with limited drug loading. Hence, it will be desirable to have formulations that are stable without the addition of excipients and also have a high drug loading.

Given the above, it would be beneficial to provide an improved or alternative method of delivery and/or drug formulation for treatment of the eye. Such a formulation would ideally enhance the benefits of therapeutic compounds such as Ranibizumab in a manner that provides a steady delivery of the therapeutic compound over a prolonged period of time. Such a formulation will utilize cationic moieties for sustained delivery minimizing antigenicity or toxicity. It will be desirable for the drug to be chemically combined with a cationic moiety for added stability, while being less toxic and antigenic than the prior art. Such a drug composition will be easy to deliver and require fewer doses over periods of time than the present therapeutic compounds for treatment of the eye.

REFERENCES

U.S. Patent Documents

U.S. Pat. No. 7,244,438 by Lingnau et al.

Other Publications

Chirila T. V. and Y. Hong, *The Vitreous Humor, in Handbook of Biomaterial Properties*, Ed. J. Black and G. Hastings, 1998, Chapman & Hall, pp. 125-131.

Doronina, S. O. et al. Development of potent monoclonal antibody auristatin conjugates for cancer therapy. *Nature Biotechnol.* 21: 778-782 (2003).

Ellman G. L. A colorimteric method for determining low concentrations of mercaptans. *Arch Biochem Biophys* 74: 443-450 (1958).

Gaudreault J. et al. Preclinical pharmacokinetics of Ranibizumab (rhuFabV2) after a single intravitreal administration, *Invest. Ophthalmol. Vis. Sci.* 46: 726-733 (2005).

Rosenfeld P. J. Intravitreal Avastin: The low cost alternative to Lucentis?, *Am. J. Ophth.* 142(1):141-143 (2006).

Singh M. P. et al. Mathematical modeling of drug release from hydrogel matrices via a diffusion coupled with desorption mechanism, *J. Cont. Rel.*, 32, 17-25 (1994).

Singh M. P. et al. Effect of electrostatic interactions on polylysine release rates from collagen matrices and comparison with model predictions, *J. Cont. Rel.*, 35: 165-179 (1995).

SUMMARY OF THE INVENTION

The present invention discloses a drug composition comprising a charged moiety chemically coupled to a therapeutic compound, wherein the charged moiety is configured to interact reversibly with at least one type of component of opposite charge in a biological tissue to create an in situ depot for prolonged drug delivery. The charged moiety may be any compound containing one or more charges such as a peptide, a combination of amino acids, or the like. The drug composition may be configured to be introduced via injection, and may contain a cationic moiety to target biological tissue (such as the eye) containing hyaluronic acid. The therapeutic compound could be a biologic, such as an anti-VEGF compound. Examples of such compounds are Ranibizumab, Bevacizumab, VEGF Trap, etc.

A method for manufacturing the drug composition is also disclosed. The method comprises chemically coupling a charged moiety to a therapeutic compound, wherein the charged moiety is configured to interact with at least one type of component of opposite charge in a human body to create an in situ depot for prolonged drug delivery. The charged moiety comprises amino acid residues, and the therapeutic compound could be an anti-VEGF compound such as Ranibizumab, Bevacizumab or VEGF Trap. The coupling is a covalent bond achieved through a chemical or genetic process.

A method of treating the human is also disclosed. The method comprises introducing into a human body a drug composition comprising a charged moiety chemically coupled to a therapeutic compound, wherein the charged moiety is configured to interact with at least one type of component of opposite charge in the human body to create an in situ depot for prolonged drug delivery. Introduction could be achieved by injecting the drug composition into any part of the body. The drug can also be introduced into any part of the body such as the eye, synovial fluid in a joint, the brain, skin, bone, cartilage or a cancerous region.

In another aspect of the invention, the therapeutic is manufactured using recombinant DNA technology wherein the therapeutic is in the form of a fusion protein comprising the therapeutically active region and the charged peptide region. The combination of the therapeutic region and the charged region provides sustained delivery of the drug to the biological tissue. Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 1*a-c* show the formation of the drug composition in accordance with two embodiments of the present invention.

DETAILED DESCRIPTION

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

The present invention is a sustained delivery dosage form to deliver therapeutic compounds to the back of the eye. Specifically, this invention discloses a drug composition formed by either covalently attaching a retaining moiety to an existing therapeutic compound, or by creating a new therapeutic compound de novo comprising charged moieties. The presence of the retaining moiety reduces the rate of the drug clearance from the target tissue, providing for sustained drug delivery.

Figure 1C:
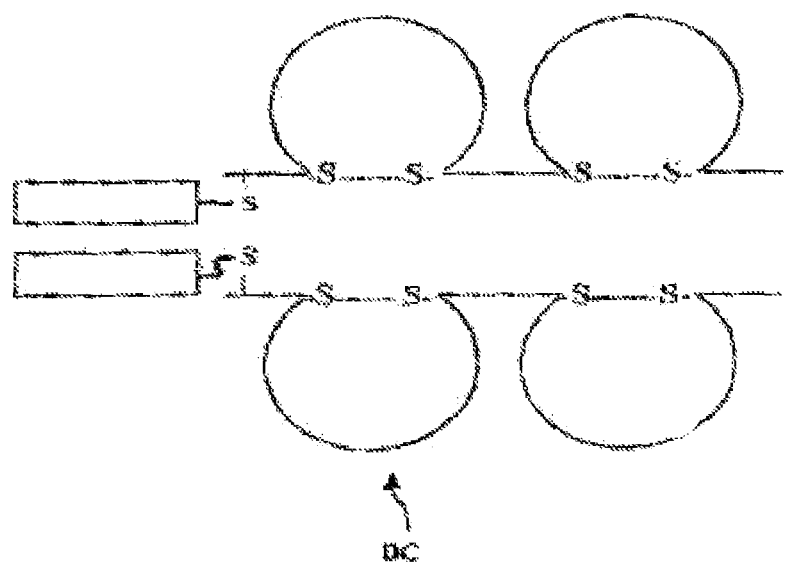

As shown in FIGS. 1a-c, the drug composition DC is formed by modifying a known therapeutic compound in such a way that it reduces the rate of clearance of the drug from the target tissue into the blood circulation. An exemplary therapeutic compound is Ranibizumab. While Ranibizumab is used as an illustrative compound, any therapeutic compound that could benefit from increased half-life and be amenable to be formulated using the methodologies described herein could benefit from this invention. Specifically, as shown in FIG. 1a, one or more retaining moieties 100 are coupled to a therapeutic compound 200 to form the drug composition DC seen in FIGS. 1b and 1c. The retaining moieties are typically cationic. However, retaining moieties may be anionic and reversibly bind to at least one type of cationic component in a biological tissue. In the preferred embodiments, the retaining moieties are cationic moieties. These cationic moieties typically comprise one or more charges formed of at least one cationic building block and are configured to reversibly bind to components of ocular tissue, such as the vitreous humor and retina, to form an in situ depot. Of course, tissues other than ocular tissue that have components amenable for reversibly binding a therapeutic composition would be appropriate delivery targets. The reversible binding slows the mass transport of the drug composition from the vitreous to the retina and subsequently to systemic circulation, resulting in an increased half-life of the therapeutic compound. Replenishment of the therapeutic compound from the depot extends the efficacy of the treatment to longer durations and, hence, reduces the frequency of intravitreal injections and their associated sight-threatening adverse events and discomfort. As an alternative to modifying a known therapeutic compound, a therapeutic compound could be formulated de novo, comprising moieties that reversibly bind to charged components of biological tissue. Regardless of whether existing therapeutic compounds are modified, or new therapeutic compounds are designed using recombinant DNA or other techniques, this invention proposes a practice opposite to the normal practice of designing proteins to avoid non-specific binding; i.e., normal protein drugs are identified and developed to achieve specific binding to receptors. The invention takes advantage of non-specific binding of therapeutics to biological tissue by modifying the therapeutic compound to enhance non-specific binding.

The drug composition of this invention, whether modified chemically or expressed using recombinant techniques, has the ability to bind to biological tissue. The binding could be assessed by performing binding experiments with excised tissue using therapeutic amounts of drug. In other words, binding is assessed with a therapeutic dose introduced to tissue or tissue components equal in size to that occurring naturally in the body (e.g., the amount of hyaluronic acid in 4.5 mL of human vitreous humor). Alternatively the size of the dose and size of the tissue or tissue components may be proportionately reduced for assessment purposes. The concentration of free compound can be determined in the supernatant after equilibration and centrifugation with or without a membrane to separate macromolecular components. Binding can also be assessed by other techniques such as spin labeling and electron spin resonance (ESR) spectra or by use of equilibrium dialysis. A repeat of the measurement at high ionic strength (e.g., 1.5 M NaCl) would release electrostatically bound compound and provide a measure of the total concentration of compound. Alternatively, the total concentration of compound is known from the preparation procedure. The fraction bound is then calculated from the previously described measurements; i.e., (Total−Free)/Total. Ideally, the preferred amount of nonspecific binding (i.e., bound fraction when using therapeutic amounts of drug) is at least 15%, more preferably, the amount of nonspecific binding is at least 25%.

Figure 2:
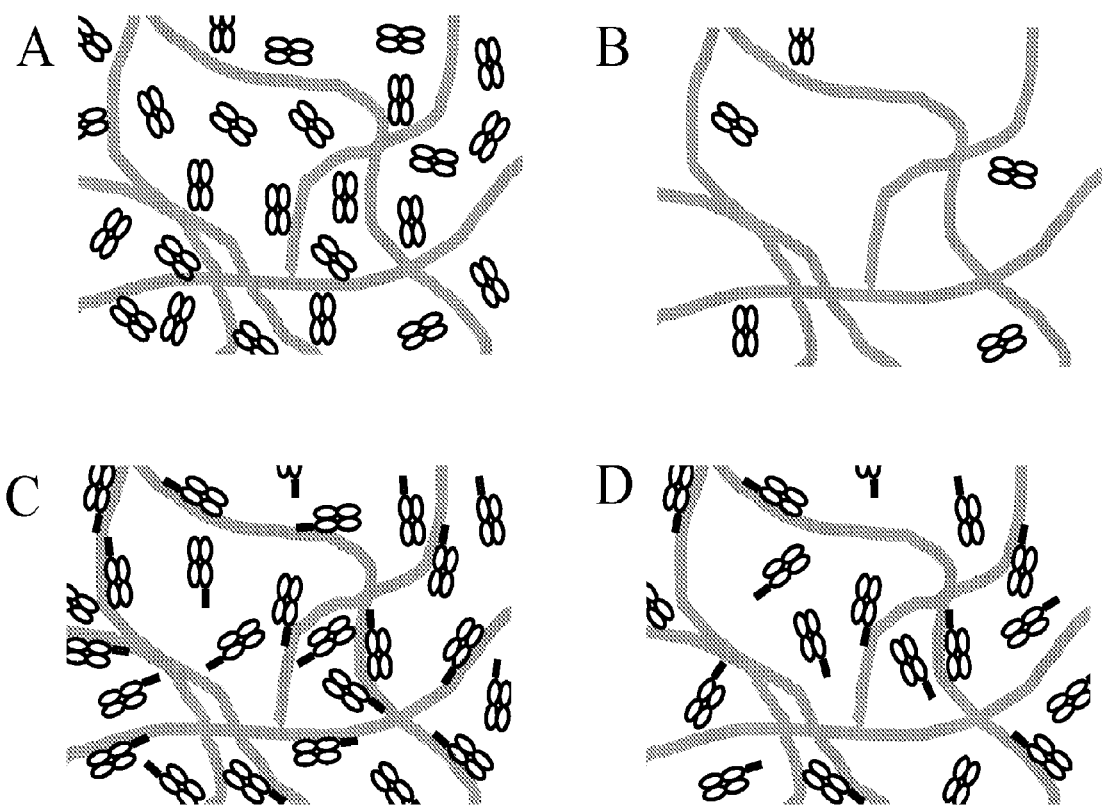
FIG. 2 shows the in vivo interaction of the drug composition with body components.

The drug composition is introduced into bodily compartments, such as the eye, exemplarily via intravitreal injection. The vitreous humor (VH) contains several vitreal components such as collagens, glycosaminoglycans, and noncollagenous structural proteins. Many of these vitreal components are negatively charged (anionic). As shown in FIG. 2, once injected into the eye, the cationic (i.e., positively charged) drug composition binds to the vitreous through electrostatic interactions with anionic (i.e., negatively charged) vitreal components, such as glycosaminoglycans (e.g., hyaluronan, also known as hyaluronic acid, chondroitin sulfate, and heparan sulfate). Additionally, other ocular tissue, such as the internal and external limiting membranes and the interphotoreceptor matrix in the neural retina, are rich in glycosaminoglycans and would also interact electrostatically with the drug compositions described in this invention. Thus, in the present invention, the vitreous serves as an in situ depot. Compared to an equal dose of therapeutic compound (e.g., Ranibizumab) without a cationic moiety, the drug concentration in the vitreous decays more slowly due to a reduction in the vitreous elimination rate. As illustrated in FIG. 2, without cationic moieties, drug from initial injection (A) is depleted relatively quickly (B). With cationic moieties, drug from initial injection (C) is still at therapeutic concentrations after a longer duration of time (D). This is due to the fact that at least some portion of the therapeutic compound, through the cationic moiety, is reversibly bound to the vitreal components. Further, since the drug composition is bound to the vitreal components, the therapeutic compound is more concentrated in the vitreous. Thus the concentration of the therapeutic compound in another part of the eye (e.g., the retina) is less than in the vitreous. The concentration in areas such as the retina is more closely related to the concentration of free drug rather than the total drug in the vitreous. This is expected to lower the maximum concentrations in the retina relative to a therapeutic compound without a cationic moiety. This drug formulation thereafter provides sustained concentrations of therapeutic compound in the retina since the bound drug composition replenishes free drug composition that has passed into systemic circulation. In this manner where the therapeutic compound is Ranibizumab, the sustained drug delivery formulation disclosed here inactivates VEGF at the site of AMD for a prolonged period of time compared to the delivery of unmodified Ranibizumab, thereby providing the desired benefit of minimizing intravitreal injections.

Turning now to the manufacturing process, the drug composition is formed by the addition of at least one cationic moiety, for example, a "tail" sequence (hereinafter also referred to as a tail) of positively charged (cationic) amino acids, to a therapeutic compound such as Ranibizumab. The therapeutic compound is exemplarily an immunoglobulin Fab (the portion of an immunoglobulin which binds to antigen) fragment comprising an H chain and L chain, with a single peptide (FIG. 1b) attached at the end of the H chain or two peptides (FIG. 1c) attached through two reduced cysteine moieties. The process of combining the cationic moieties to the fragment is achieved via a chemical process (e.g., adding peptide to Ranibizumab by reaction with α-amino group or reduced cysteines of the fragment via hydroxysuccinimide or maleimide coupling, respectively; see FIGS. 1b and 1c, respectively) or genetic process (e.g., construction of a fusion protein in which the peptide is fused to the C-terminus of the Fab H chain sequence; see FIG. 1b).

In the case of a chemical process, peptides are attached chemically to sites along the H and L chains. Synthetic peptides can be attached to a variety of sites on the therapeutic protein. In addition to the N- and C-termini, attachment can be via side chains of accessible lysines, cysteines, cystines, glutamic and aspartic acid, other potentially reactive amino acids, as well as oxidized carbohydrate moieties of oligosaccharides. Conjugation of peptides to protein is performed on proteins synthesized separately from the peptide, then combined. In this scenario, peptides can form branch points in the amino acid sequence of the therapeutic protein, either by attachment to a side chain, or by the use of a branched synthetic peptide. Alternatively, peptides may be added site-specifically to native disulfide bonds (cystines, or following reduction, cysteines) of therapeutic proteins. Further, because the number of disulfides in Fab molecules is limited and the reaction appears to be efficient, stoichiometric addition may be utilized. In addition to Fab molecules, full length monoclonal antibodies can be modified by addition of peptide "tails" using similar approaches.

The tail is covalently attached to the therapeutic compound by any suitable process that is well known in the art. The preferred sites of attachment on the therapeutic protein are amino and sulfhydryl groups. Typically, an amino group (N-terminal α-amino group of H or L chain or ϵ-amino groups of lysines) on the therapeutic compound is combined with the carboxyl terminus of the tail via a group such as N-hydroxysuccinimide to form an amide bond. Alternatively, succinimidyl succinate, glutarate or carbonate can be used to form a more labile ester bond with amines. The resulting labile bond is cleaved by esterases found naturally in ocular and other tissues. Cleavable ester linkages are often utilized with prodrugs such as dexamethasone sodium phosphate. Sulfhydryl groups on the therapeutic compound can also be used as sites of attachment. Treatment with a reducing agent (dithiothreitol, tris(2-carboxyethyl) phosphine) can reduce disulfide bonds to generate free cysteines, with subsequent reaction of the sulfhydryls with m-maleimidobenzoyl-N-hydroxysuccinimide-derivatized peptide tail. For cleavable linkages such as esters, additional moieties may be added to provide steric hindrance in order to slow down and achieve the desired kinetics of conversion. Beyond the linking chemistry, the kinetics of release of the therapeutic compound can be tuned by modulating the length and composition of the cationic tail and thereby varying the binding affinity of the tail for the charged component in biological tissue.

The following example illustrates the conjugation of cationic peptide to a therapeutic compound such as AVASTIN® (Bevacizumab) by using a reactive end such as m-maleimidobenzoyl-N-hydroxysuccinimide ester (MBS) at the N-terminus of the synthetic peptide tail. The example should not be construed as limiting.

Example 1

Conjugation of Cationic Peptide "Tails" to Bevacizumab

The following exemplary maleimide-derivatized cationic peptides were custom-synthesized by HyBio (Shenzhen, China):
(MBS)-KGSKGSKGSKGSK-NH$_2$ (SEQ ID NO:1)
(MBS)-KGKSKGKSK-NH$_2$ (SEQ ID NO:2)
(MBS)-KGSKGSK-NH$_2$ (SEQ ID NO:3)
(MBS)-KGKSK-NH$_2$ (SEQ ID NO:4)
Where
  K=lysine
  G=glycine
  S=serine
  MBS=N-terminal m-maleimidobenzoyl-N-hydroxysuccinimide ester
  NH$_2$=C-terminal amide Each peptide contains 3 or 5 lysine groups separated by flexible spacers of 1-2 neutral amino acids in order to achieve more optimal spacing of charges to match with the spatial arrangement of charges present on the repeating disaccharide units in hyaluronic acid (see FIG. 3). AVASTIN® (Bevacizumab) was obtained from Genentech, Inc., (South San Francisco, Calif.); dithiothreitol (DTT), N-acetylcysteine, ethylenediaminetetraacetic acid (EDTA), 5,5'-dithiobis(2-nitrobenzoic acid) (DTNB), and all other chemicals were from Sigma (St. Louis, Mo.).

Chemical Reduction of Bevacizumab

The method used was based on that described by Doronina et al. (2003). Bevacizumab (5 mg) at 5 mg/mL was incubated in 50 mM borate pH 8.0 with 10 mM DTT for 30 minutes at 37° C. to reduce disulfide bonds. Reduced protein was recovered free of excess DTT using Econo 10G columns (BioRad) equilibrated in phosphate-buffered saline containing 1 mM ETDA. The presence of free thiols in DTT-treated Bevacizumab (approx. 3 mg at 2 mg/mL) was confirmed using the DTNB assay (Ellman 1958).

Conjugation with M-Maleimidobenzoyl-N-Hydroxysuccinimide Ester (MBS)-Derivatized Peptides Immediately before use, MBS peptides were dissolved in water to make 20 mM stock solutions. MBS-peptides (16 μL) were added to 1.6 mL of reduced Bevacizumab, (MBS peptides were in 20× molar excess over Bevacizumab). Mixtures were incubated for 1 hour at 4° C. to allow MBS-peptides to react with free thiols on Bevacizumab. After 1 hour, the reaction was quenched with excess N-acetylcysteine (15 μL of 62 mM), 10 min at 4° C., and peptide-Bevacizumab conjugates were recovered free of excess peptides using Econo 10G columns equilibrated in Dulbecco's phosphate-buffered saline. The amount of Bevacizumab recovered (approx. 2.5 mg at 1.4 mg/mL) was then determined using the Micro BCA assay (Pierce Thermo Scientific, Rockford, Ill., Cat. No. 23235). This chemical reduction protocol was intended to generate free thiols from only interchain disulfide bonds. If all of the free thiols participate in conjugation, then there are 8 peptides conjugated to each Bevacizumab molecule.

In the case of a genetic process, one or two peptides per fragment are attached at the ends of one or both of the H and L chains. Alternatively, peptides may be incorporated de novo into the therapeutic protein via design and production of a recombinant fusion protein, in which a gene encoding the peptide fused to the protein is used to express the fusion protein. The fusion protein is designed so that the peptide can be attached at the N- or C-terminus, or embedded within the internal sequence of the protein. In this scenario, the peptide is co-linear with the therapeutic protein and can be present in individual copies or in tandem repeats.

The cationic tail is configured to bind to components of the desired tissue target site without specificity. However, the length and sequence of the peptide may be configured for optimal binding affinity to specific components such as hyaluronic acid. The peptide may be 2-30 amino acid residues in length, and may contain an abundance of basic residues (Arg, Lys, His). Amino acid residues not involved in hyaluronan binding (e.g., glycine, serine) can be added to the sequence, if needed, to provide proper spacing for the charges on the retaining peptide.

Various cationic building blocks may be used in formulating the therapeutic compound with a multivalent cationic retaining moiety. Such building blocks include amino acids that are positively charged at physiologic conditions, including those naturally occurring amino acids such as lysine, histidine, and arginine. The cationic moiety may be configured to mimic hyaluronan-binding proteins (such as CD44) in terms of composition and spatial arrangement of amino acids. Various other chemical species can be used for the retaining cationic moiety. These include polycations containing the building blocks of polymers used to form polyplexes and lipoplexes in gene delivery, such as polyethylenimine, polyamidoamine, spermine, DOTAP, and polymers derivatized with imidazole-containing pendant groups. That is, polycations that have been used in nonviral gene therapy systems are also applicable to this invention. As previously mentioned in the background section, polycations such as polyethylenimine and polylysine are utilized in nonviral gene delivery systems to protect nucleic acid therapeutics (e.g., DNA and siRNA) from degradation and facilitate uptake into cells. With respect to the preferred embodiment of the present invention, the process is intended to encourage the cationic moiety to form an in situ depot of molecularly dispersed, soluble protein that has reduced elimination rates due to reversible, non-specific binding with biological tissue. Various anionic building blocks may be used to create an anionic retaining moiety. Examples include negatively charged amino acids, such as aspartic acid and glutamic acid, or other negatively charged chemical species such as bisphosphonates (e.g., boniva and actenol).

Other usable building blocks include biodegradable chemical species, such as the polyester poly[α-(4-aminobutyl)-L-glycolic acid] and poly(β-amino esters). Additionally, the building blocks may contain other types of multivalent cations, such as the multivalent metal ions calcium and iron.

In one embodiment, at least one cationic moiety of 2-30 lysine residues is used, more preferably 3-10 lysine residues. Each addition of a cationic building block enables an additional electrostatic interaction with the anionic components in biological tissue. Increasing the number of building blocks, and thus the number of interactions, will increase the binding strength with a relationship that is stronger than linear. Thus the cationic moiety has less cationic building blocks than required for complete immobilization, so that complexation is reversible in a timeframe that achieves a sustained rate of a therapeutic dose. Simultaneously, the cationic moiety will comprise a charge density that is both of low antigenicity and toxicity.

The following examples illustrate the advantage of increasing the number cationic building blocks (exemplarily denoted as poly-L-lysine hydrobromide) to binding with anionic components in biological tissue (exemplarily denoted as hyaluronic acid). The examples should not be construed as limiting.

Example 2

Binding of Poly-L-Lysine Hydrobromide Comprising More than 72 Lysine Groups Per Chain to Hyaluronic Acid This experiment measured binding of poly-L-lysine hydrobromide to hyaluronic acid (HA). Poly-L-lysine hydrobromide was obtained from Sigma (P7890), denoted herein as 22K pLys. This sample has a molecular weight range of 15,000-30,000 Da based upon viscosity measurements, corresponding to 72-144 lysine groups per chain.

Hyaluronic acid potassium from human umbilical cord was also purchased from Sigma (H1504). HA has a molecular weight of about 3,500,000 Da. Human vitreous contains 100-400 ug/mL hyaluronic acid. (T. V. Chirila and Y. Hong, The Vitreous Humor, in Handbook of Biomaterial Properties, Ed. J. Black and G. Hastings, 1998, Chapman & Hall, pp. 125-131.) It has an electrolyte composition generally similar to human plasma. All test solutions were prepared with Dulbecco's phosphate buffered saline (DPBS) from Sigma (D8662).

A series of samples was prepared with varying amounts of 22K pLys and a constant amount, 500 ug/mL, of hyaluronic acid potassium. These samples were equilibrated at room temperature for at least 15 minutes. Centrifugal filtration units (Amicon Ultra-4 Ultracel-50K, Millipore) with a 50 kDa molecular weight cutoff were used to separate pLys bound to hyaluronic acid from the free pLys in solution. These were processed in a clinical centrifuge (IEC Model CL) at a setting of 4 for at least 10 minutes. The concentration of free pLys was measured in the filtrate by trinitrobenzenesulfonic acid (TNBS) assay. Samples were run in a 96 well and read at 420 nm on a Molecular Dynamics VersaMax plate reader.

A solution containing 37.5 ug/mL of 22K pLys with no hyaluronic acid was tested in order to verify that pLys would pass though the 50 kDa MW cutoff membrane. The concentration of pLys in the filtrate was 35.5 ug/mL. The result indicates that this method should be sufficient to separate free pLys from pLys bound to HA.

A solution containing 500 ug/mL of HA (no pLys) was also included as a control. The TNBS signal for the filtrate of this sample was less than the lowest standard (1 ug/mL pLys) and similar to values obtained for blank DPBS. Hence, there were no protein impurities from hyaluronic acid detected.

Figure 4:
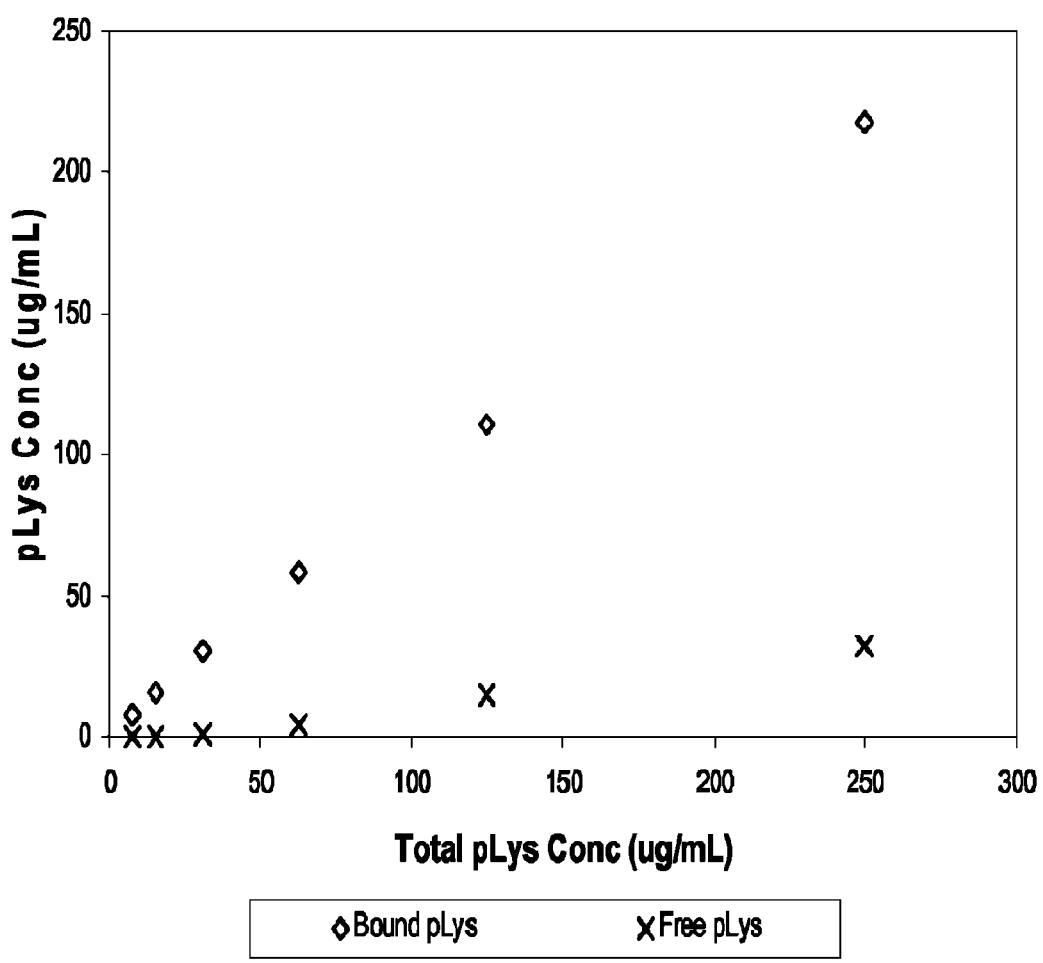
FIG. 4 shows the concentration of bound and free 22 kDa polylysine as a function of total polylysine concentration for solutions containing 500 ug/mL hyaluronic acid.

FIG. 4 shows the concentration of free 22K pLys measured as a function of total pLys concentration for solutions containing 500 ug/mL hyaluronic acid. The amount of pLys bound to HA was calculated by subtracting the free pLys concentration from the total pLys concentration. The majority of 22K pLys was bound to hyaluronic acid in the presence of physiologic electrolyte concentrations.

Example 3

Binding of pLys to a Lower Concentration of Hyaluronic Acid

Since, the methodology in Example 3 is limited by precipitation of 22K pLys samples were prepared for binding to a lower concentration, 250 ug/mL, of hyaluronic acid potassium in order to extend the results to a higher ratio of pLys/HA.

Figure 5:
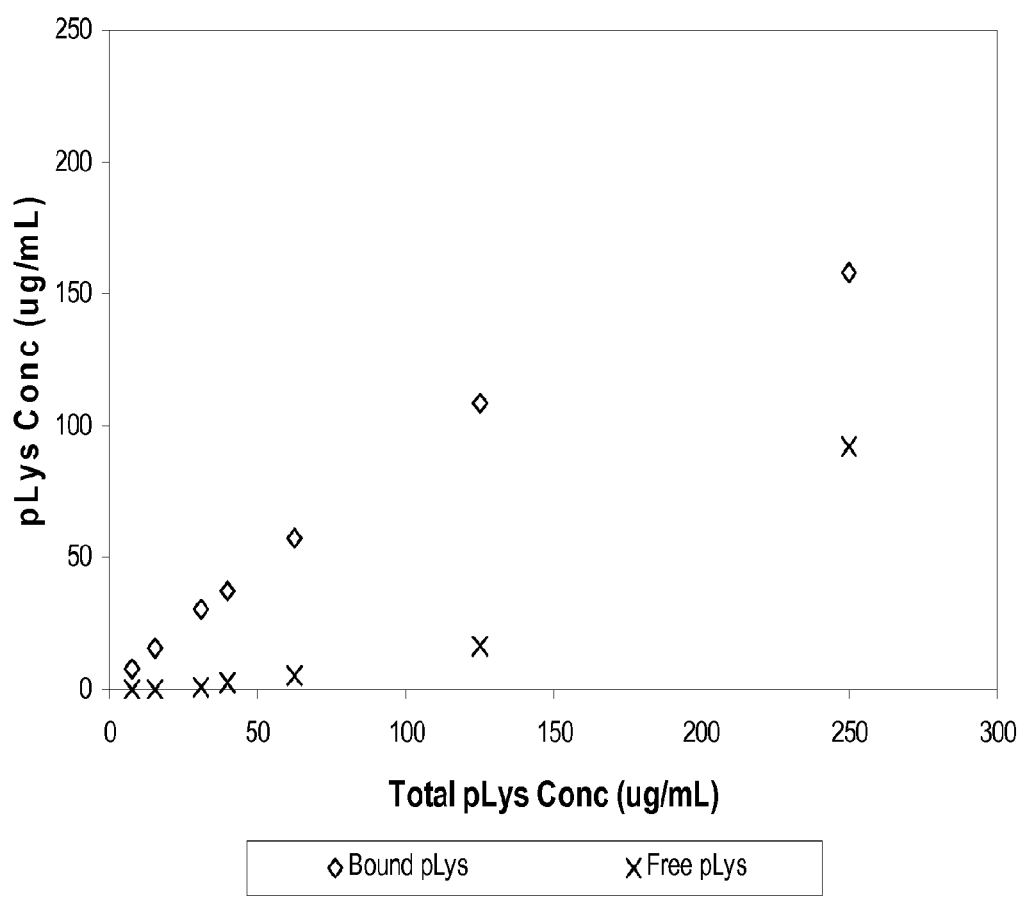
FIG. 5 shows the concentration of bound and free 22 kDa polylysine as a function of total polylysine concentration for solutions containing 250 ug/mL hyaluronic acid.

FIG. 5 shows the concentration of bound and free 22K pLys as a function of total pLys concentration for solutions containing 250 ug/mL hyaluronic acid.

Figure 6:
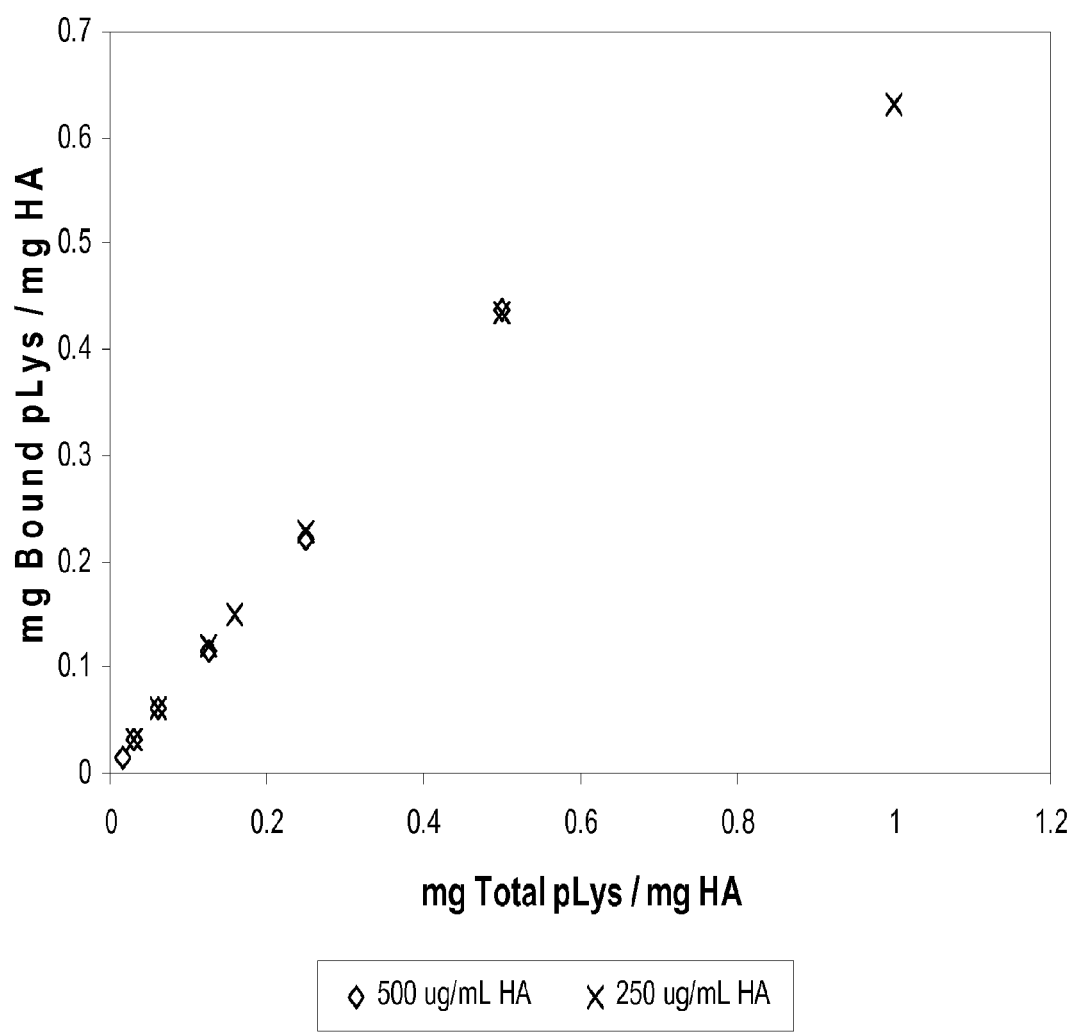
FIG. 6 displays the ratio of mg bound polylysine to mg hyaluronic acid for solutions of 22 kDa polylysine as described in Examples 2 and 3.

FIG. 6 displays data from Examples 2 and 3. The amount of bound pLys per mg of HA is dependent on the total amount of pLys per mg of HA. Hyaluronic acid is saturated with 22K pLys at amounts higher than 0.65 mg pLys per mg HA.

Example 4

Binding of pLys of Lower Molecular Weight to Hyaluronic Acid

Binding experiments were performed with a lower molecular weight poly-L-lysine using the methodology described in Example I. Poly-L-lysine hydrobromide was obtained from Sigma (P0879), denoted herein as 3K pLys. This sample has a molecular weight range of 1,000-5000 Da based upon viscosity measurements, corresponding to 5-24 lysine groups per chain. Solutions contained 0, 250, or 500 ug/mL hyaluronic acid potassium.

A control containing 31.3 ug/mL of 3K pLys with no hyaluronic acid was included in this experiment. The concentration of pLys in the filtrate was 31.8 ug/mL, indicating that free 3K pLys should be easily separated from HA and 3K pLys bound to HA.

Figure 7:
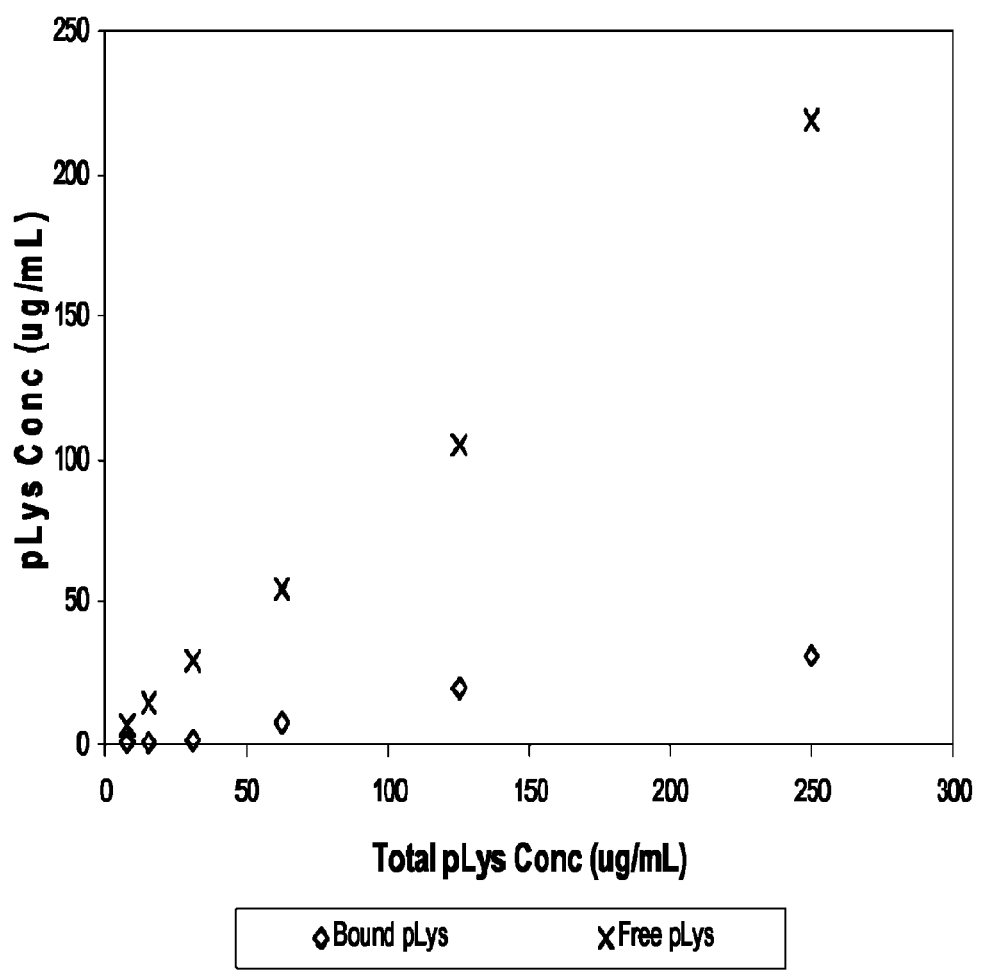
FIG. 7 shows the concentration of bound and free 3 kDa polylysine as a function of total polylysine concentration for solutions containing 500 ug/mL hyaluronic acid.

FIG. 7 shows the concentration of free 3K pLys measured as a function of total pLys concentration for solutions containing 500 ug/mL hyaluronic acid. The amount of pLys bound to HA was calculated by subtracting the free pLys concentration from the total pLys concentration. The majority of the 3K pLys was free in solutions of hyaluronic acid in the presence of physiologic electrolyte concentrations.

Figure 8:
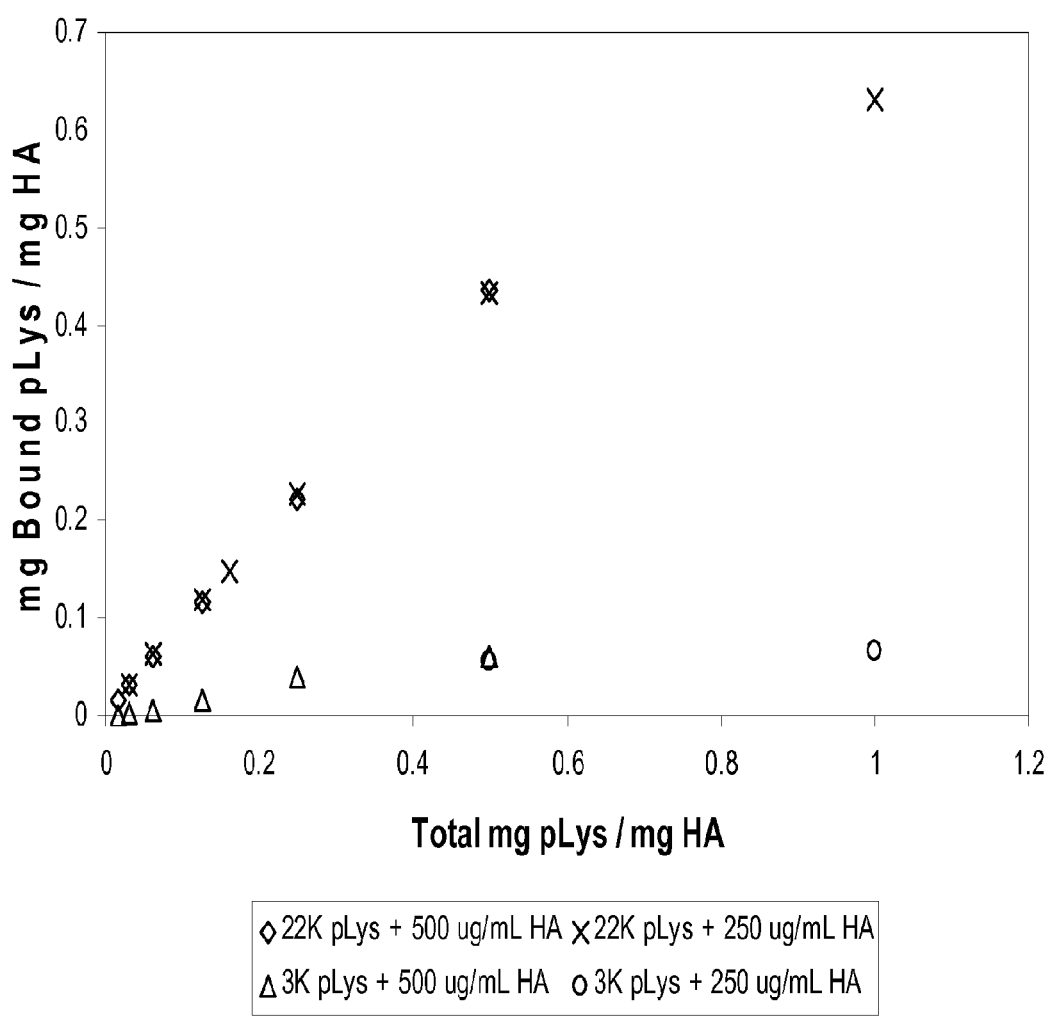
FIG. 8 displays the ratio of mg bound poly-Lysine to mg hyaluronic acid for solutions of 3 polylysine and 22 kDa polylysine as described in Examples 2, 3, and 4.

FIG. 8 illustrates the data overlays from Examples 2, 3, and 4. For both 3K pLys and 22K pLys, the amount of bound pLys per mg of HA is dependent on the total amount of pLys per mg of HA. While the saturation level was greater than 0.65 mg pLys per mg HA for 22K pLys, the saturation level is only approximately 0.06 mg pLys per mg HA for 3K pLys. These data demonstrate that increasing the number of lysine groups increases the amount of polylysine that binds to hyaluronic acid in a buffer that is representative of physiological conditions.

Figure 3:
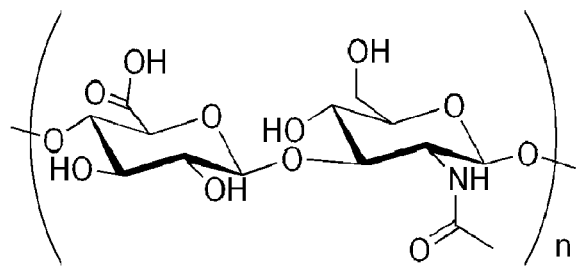
FIG. 3 shows an exemplary building block in accordance with one embodiment of the present invention.
Figure 3:
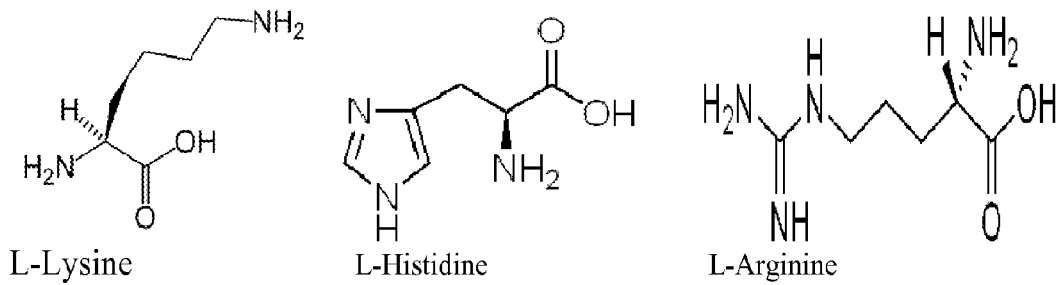
Figure 3:
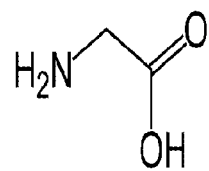

The charged moieties may comprise any architecture or formation. For example, they may be linear, branched, or dendritic. They may contain neutral, flexible spacers at the location where the moiety is attached to the therapeutic compound in order to facilitate close proximity between the charges of the retaining moiety building blocks and the opposite charges of the biological tissue. Similarly, it may be advantageous to include neutral, flexible spacers between the building blocks to enable optimal spatial matching of charges on the building blocks and opposite charges on the biological tissue. For example, hyaluronic acid is negatively charged when the carboxyl groups on the glucuronic acid moiety are dissociated. As shown in FIG. 3, these carboxyl groups occur once on each repeating disaccharide unit. Since the length of a disaccharide unit is greater than the length of an amino acid unit in a peptide, uncharged flexible spacers enable better spatial matching between positive and negative charges. Examples of preferred flexible spacers are neutral amino acids without bulky or strongly interacting side chains, such as stretches of glycine, alanine and serine.

The rate of drug delivery from the vitreous to the retina is dependent on the rate of desorption from the anionic components in the biological tissue and the rate of mass transport through the vitreous. Drug reaches the retina by a combination of diffusive and convective processes, the latter involving water flow driven by the hydraulic pressure associated with the production of aqueous humor by the ciliary body. Drug elimination rates are strongly dependent on the size of the drug, with diffusion playing a more significant role for small molecules and convection dominating for large molecules. The presence of charged retaining moieties will slow the rate of both diffusion and convection. Additionally, delivery can be prolonged further if desorption is slow compared to the time scale of mass transport. The kinetics of release from the in situ depot can be tuned by modulating the composition and length of the retaining moiety and the number of retaining moieties attached to each molecule to vary binding affinity. This, in turn, will impact desorption rates and reduce the rates of diffusion and convection.

The following examples illustrate binding of cationic peptide conjugated therapeutic compounds such as peptide-Bevacizumab to hyaluronic acid. These examples should not be construed as limiting.

Example 5

Non-Binding of Non-Conjugated Bevacizumab Avastin to Hyaluronic Acid

The methodology for determining free concentrations of peptide-Bevacizumab-conjugates from peptide-Bevacizumab conjugates bound to hyaluronic acid was developed using Bevacizumab; i.e., no conjugation. Eequilibrium dialysis cells (Harvard Apparatus) were used with a 0.03 μm pore size polycarbonate membrane (Whatman, Nuclepore track-etched Cat No. 110602), as centrifugal filtration units were not available with a pore size that would allow passage of the 150 kDa protein. The cells have interchangeable parts with chamber capacities of 250 or 500 μL achieved by changing area while holding the depth from the membrane surface constant.

Experiments were performed by filling the donor chamber with a known amount of Bevacizumab in DPBS and filling the receiver with DPBS. For these experiments, the donor and receiver chambers had equal volumes. The solutions were allowed to equilibrate for the amount of time specified in Table 1. Then the solutions were removed from the chambers and assayed for Bevacizumab concentration measured via protein assay (Micro BCA).

The concentration of Bevacizumab in the receiver was within approximately 25% of the concentration in the donor after about 2 days. Hence, equilibration times greater than two days were needed to measure free protein in equilibrium with the donor solution when the donor and receiver chambers have equal volumes. The second experiment included donor solutions containing Bevacizumab and hyaluronic acid. Similar results were obtained from donor solutions with and without hyaluronic acid, indicating similar concentrations of free protein irrespective of the presence of hyaluronic acid. In other words, the results suggested the amount of Bevacizumab bound to hyaluronic acid was close to zero.

TABLE 1

Binding of Bevacizumab to hyaluronic acid

| Experiment | Equilibration Time (hr) | Bevacizumab Conc (µg/mL) | HA Conc (µg/mL) | Bevacizumab Conc in Donor Side (% of Loading) | Bevacizumab Conc in Receiver Side (% of Loading) | Receiver/Donor |
|---|---|---|---|---|---|---|
| 1 | 44 | 500 | 0 | 56% | 44% | 78% |
| 2 | 46 | 250 | 0 | 58% | 42% | 73% |
| 2 | 46 | 250 | 0 | 56% | 44% | 80% |
| 2 | 46 | 250 | 500 | 54% | 46% | 86% |
| 2 | 46 | 250 | 500 | 57% | 43% | 74% |
| 2 | 46 | 250 | 500 | 57% | 43% | 76% |

Example 6

Binding of Cationic Peptide-Bevacizumab Conjugates to Hyaluronic Acid

The membranes and equilibrium dialysis cells described in Example 5 were then used to separate free peptide-Bevacizumab conjugates from peptide conjugates bound to hyaluronic acid.

The mAb-peptide conjugates as conjugated by the process described in Example 1 were designated as follows and were analyzed for binding to hyaluronic acid.

| Compound ID | Compound Description |
|---|---|
| Pep-Bevacizumab 1 | Bevacizumab-S-[KGSKGSKGSKGSK-NH2] (SEQ ID NO: 1) |
| Pep-Bevacizumab 2 | Bevacizumab-S-[KGKSKGKSK-NH2] (SEQ ID NO: 2) |
| Pep-Bevacizumab 3 | Bevacizumab-S-[KGSKGSK-NH2] (SEQ ID NO: 3) |
| Pep-Bevacizumab 4 | Bevacizumab-S-[KGKSK-NH2] (SEQ ID NO: 4) |
| Bevacizumab | Bevacizumab |

The peptide-Bevacizumab conjugates were diluted in a 1:3 ratio with a solution of 1 mg/mL HA in DPBS. The donor chambers of the equilibrium dialysis cells were filled with 500 µL of these mixtures while the receiver chambers were filled with 500 µL of DPBS. After an equilibration time of 3.7 days, two 50 µL aliquots were removed from each chamber and assayed by Micro BCA to determine the concentration of peptide-Bevacizumab conjugates. Independent control solutions of each peptide-Bevacizumab-conjugate in solution with or without HA indicate that the presence of HA does not interfere with the ability of Micro BCA to quantitate the concentration of peptide-Bevacizumab-conjugate. In addition, a mass-balance check of bound and free peptide-Bevacizumab-conjugate in the donor chamber and free peptide-Bevacizumab conjugate in the receiver chamber was within 3% of the amount of free peptide-Bevacizumab conjugate loaded in the donor chamber.

A second set of aliquots was removed after 6.7 days of equilibration. The results are shown in Table 2 and 3 for equilibration of 3.7 and 6.9 days, respectively.

The small change in concentrations between samples taken at 3.7 and 6.9 days suggested that the latter samples were close to equilibrium. The concentrations measured in the receiver chambers provided the amounts of free peptide-Bevacizumab conjugate. The difference between the donor and receiver concentrations provided the amount of peptide-Bevacizumab conjugate bound to hyaluronic acid. The Fraction Bound is the ratio of bound peptide-Bevacizumab conjugate to the total peptide-Bevacizumab conjugate. The ratio of mg pep-Bevacizumab bound to mg HA is also shown for the final equilibrated donor chamber.

The peptides with 5 lysines (Pep-Bevacizumab 1 and 2) had a higher fraction bound to hyaluronic acid than the peptides with 3 lysines (Pep-Bevacizumab 3 and 4). This demonstrated that increasing the amount of charge on the peptide chains increased the binding affinity.

TABLE 2

Equlibration for 3.7 days

| Pep-Bevacizumab | Peptide sequence | Initial Pep-Bevacizumab Donor Conc (µg/mL) | HA Conc in Donor (µg/mL) | Free Pep-Bevacizumab (µg/mL) | Bound Pep-Bevacizumab (µg/mL) | Fraction Bound | Mg Bound Pep-Bevacizumab/ mg HA | mg Total Pep-Bevacizumab/ mg HA in Donor |
|---|---|---|---|---|---|---|---|---|
| 1 | KGSKGSKGSKGSK-NH2 (SEQ ID NO: 1) | 371 | 750 | 44 | 286 | 0.87 | 0.38 | 0.44 |
| 2 | KGKSKGKSK-NH2 (SEQ ID NO: 2) | 373 | 750 | 39 | 299 | 0.88 | 0.40 | 0.45 |
| 3 | KGSKGSK- NH2 (SEQ ID NO: 3) | 414 | 750 | 131 | 151 | 0.53 | 0.20 | 0.38 |
| 4 | KGKSK-NH2 (SEQ ID NO: 4) | 408 | 750 | 143 | 131 | 0.48 | 0.18 | 0.37 |
| 5 | None (Bevacizumab-only) | 403 | 750 | 192 | 29 | 0.13 | 0.04 | 0.29 |

TABLE 3

Equlibration for 6.9 days

| Pep-Bevacizumab | Peptide sequence | Initial Pep-Bevacizumab Donor Conc (μg/mL) | HA Conc in Donor (μg/mL) | Free Pep-Bevacizumab (μg/mL) | Bound Pep-Bevacizumab (μg/mL) | Fraction Bound | Mg Bound Pep-Bevacizumab/ mg HA | mg Total Pep-Bevacizumab/ mg HA in Donor |
|---|---|---|---|---|---|---|---|---|
| 1 | KGSKGSKGSKGSK-NH2 (SEQ ID NO: 1) | 371 | 750 | 49 | 275 | 0.85 | 0.37 | 0.43 |
| 2 | KGKSKGKSK-NH2 (SEQ ID NO: 2) | 373 | 750 | 46 | 298 | 0.87 | 0.40 | 0.46 |
| 3 | KGSKGSK-NH2 (SEQ ID NO: 3) | 414 | 750 | 140 | 126 | 0.47 | 0.17 | 0.36 |
| 4 | KGKSK-NH2 (SEQ ID NO: 4) | 408 | 750 | 142 | 113 | 0.44 | 0.15 | 0.34 |
| 5 | None (Bevacizumab-only) | 403 | 750 | 192 | 21 | 0.10 | 0.03 | 0.28 |

Example 7

Determination of Non-Specific Binding of Cationic Peptide-Bevacizumab Conjugates to Hyaluronic Acid Intravitreal injections of 1.25 mg AVASTIN® (Bevacizumab) are commonly given off-label to treat age-related macular degeneration (Rosenfeld, *Am. J. Ophth.* 142(1):141-143, 2006). An additional binding experiment was performed with less hyaluronic acid to determine the amount of nonspecific binding that occurs for an intravitreal injection of a therapeutic dose of Bevacizumab into a human eye. A human eye has 0.45-1.8 mg HA (4.5 mL of vitreous containing 0.1-0.4 mg/mL HA). Therefore, it is of interest to characterize the amount of nonspecific binding for concentrations in the range of 0.7 to 2.7 mg total peptide-Bevacizumab conjugate/mg HA.

This experiment used equilibrium dialysis cells with 500 μL donor chambers and 250 μL receiver cells in order to shorten the time needed for free peptide-Bevacizumab-conjugate to diffuse across the membrane and reach equilibrium between the donor and receiver chambers. The results are shown in Table 4 after 3.0 days of equilibration. Again, higher binding affinity was observed for peptide-Bevacizumab conjugates with 5 lysines per peptide (Pep-Bevacizumab 1 & 2) compared to 3 lysines per peptide (Pep-Bevacizumab-3 & 4). In addition, comparing Examples 6 and 7, the conjugates with peptides containing single flexible spacers (Pep-Bevacizumab 2 & 4) are more differentiated from conjugates with two flexible spacers (Pep-Bevacizumab 1 & 3). When there was more drug per HA, the conjugates with peptides containing single flexible spacers had a higher fraction bound (i.e., higher binding affinity) than conjugates containing two flexible spacers.

The custom peptides were selected based on the hypothesis that separating the lysines would enable better electrostatic complexation with HA due to the fact that HA has one negative charge every other ring structure. Peptides such as polylysine without spacers would have extra charges that would not match up with charges on HA. The extra charges might favor desorption into aqueous solution while neutral spacers might promote stronger binding affinity through hydrophobic interactions in addition to electrostatic complexation of the better spatially matched ions. The results here suggested the peptides with single neutral amino acid spacers had a more optimal spatial arrangement for complexation with HA than peptides with two neutral amino acid spacers.

Note that more complete equilibration may yield slightly lower fractions bound. Data in Tables 2 through 4 indicate that fraction of Bevacizumab bound to hyaluronic acid (i.e., non-specific binding at therapeutic concentrations) is approximately 0.1 or less.

TABLE 4

Non-specific binding of Pep-Bevacizumab to hyaluronic acid

| Pep-Bevacizumab | Peptide sequence | Initial Pep-Bevacizumab Donor Conc (μg/mL) | HA Conc in Donor (μg/mL) | Free Pep-Bevacizumab (μg/mL) | Bound Pep-Bevacizumab (μg/mL) | Fraction Bound | Mg Bound Pep-Bevacizumab/ mg HA | mg Total Pep-Bevacizumab/ mg HA in Donor |
|---|---|---|---|---|---|---|---|---|
| 1 | KGSKGSKGSKGSK-NH2 (SEQ ID NO: 1) | 601 | 567 | 158 | 305 | 0.66 | 0.54 | 0.82 |
| 2 | KGKSKGKSK-NH2 (SEQ ID NO: 2) | 525 | 567 | 98 | 421 | 0.81 | 0.74 | 0.91 |
| 3 | KGSKGSK-NH2 (SEQ ID NO: 3) | 581 | 567 | 295 | 214 | 0.42 | 0.38 | 0.90 |
| 4 | KGKSK-NH2 (SEQ ID NO: 4) | 572 | 567 | 220 | 270 | 0.55 | 0.48 | 0.87 |
| 5 | None (Bevacizumab-only) | 517 | 567 | 361 | 43 | 0.11 | 0.08 | 0.71 |

Example 8

Delivery Rates from Cationic Peptide-Bevacizumab Avastin Conjugates to Hyaluronic Acid The same 0.03 μm pore size membranes and equilibrium dialysis cells used in Examples 5 through 7 were used as permeation cells to measure delivery rates from peptide-Bevacizumab conjugates electrostatically complexed to hyaluronic acid. The donor chambers were filled with 240 μL of peptide-Bevacizumab conjugate and hyaluronic acid, while the receiver chambers were filled with 480 μL of DPBS. Initially twice a day, the receiver chambers were completely replaced with DPBS to assess delivery rates with close to sink conditions in the receiver. The concentrations of peptide-Bevacizumab-conjugate in the initial donor solutions and the receiver solutions were determined by Micro BCA. The donor solutions contained 500 μg/mL HA and initially had an average of 675 μg/mL peptide-Bevacizumab conjugate, corresponding to an average loading of 160 μg of peptide-Bevacizumab conjugate in the 240 μL donor. The donors contained a physiologically relevant amount of drug to HA, 1.35 mg total peptide-Bevacizumab conjugate/mg HA.

Figure 9:
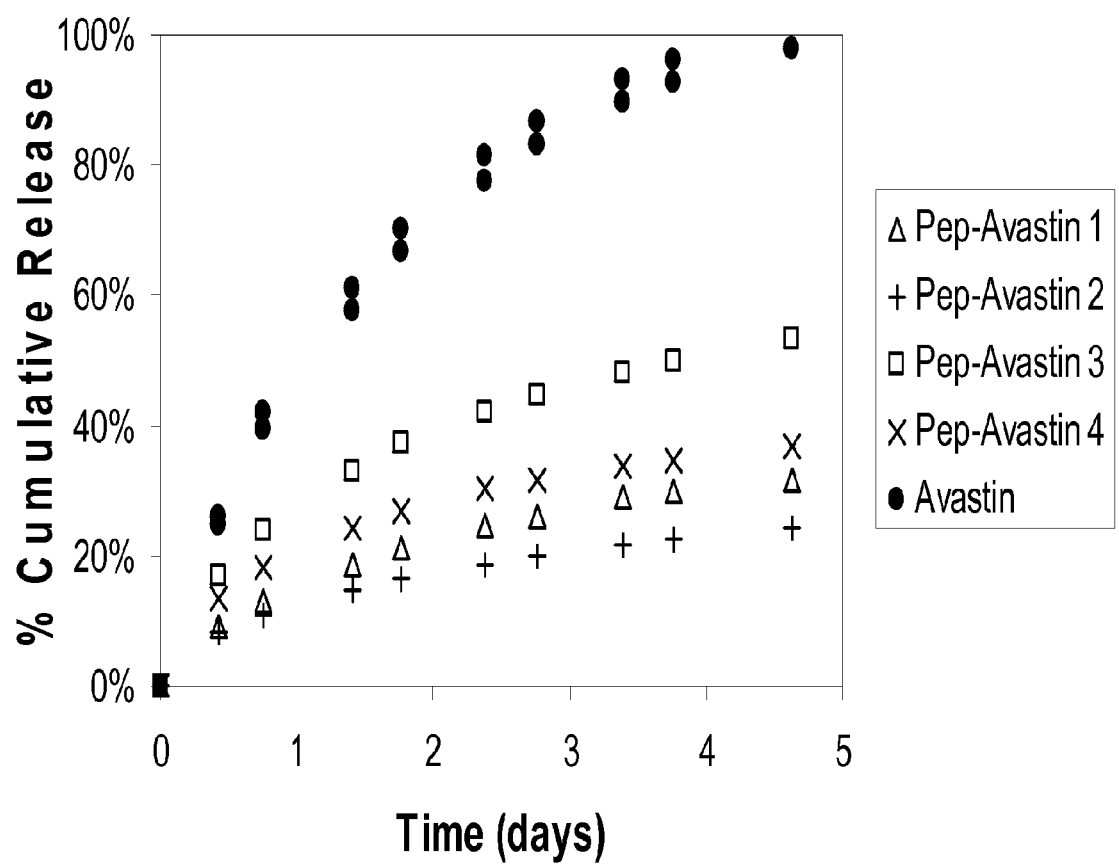
FIG. 9 displays the cumulative delivery of peptide Bevacizumab conjugates versus non-conjugated Bevacizumab.
Figure 10:
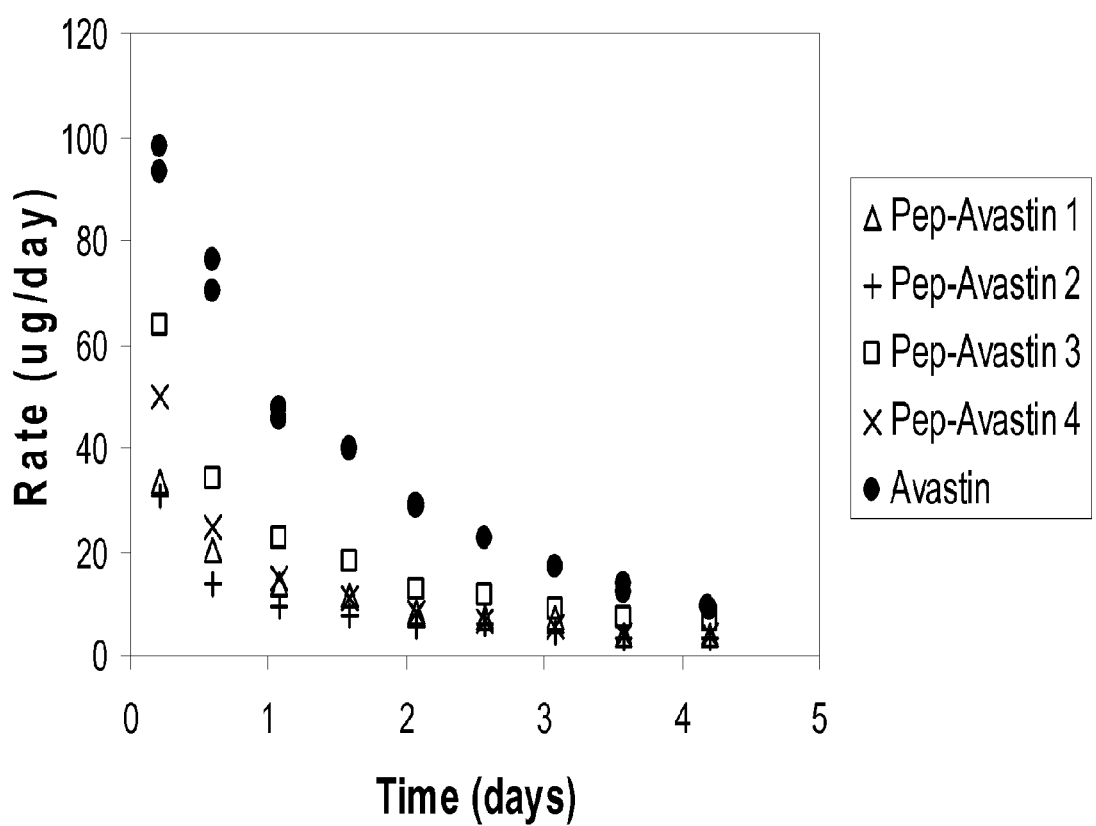
FIG. 10 shows the delivery rates of the four exemplary peptide Bevacizumab conjugates versus non-conjugated Bevacizumab.

FIG. 9 displays the cumulative delivery of peptide-Bevacizumab conjugates. FIG. 10 shows delivery rates of the four peptide-Bevacizumab conjugates versus Bevacizumab. The rates were normalized to a loading of 160 μg in order to remove the impact of small variations in donor concentrations from the results.

Slower release kinetics are observed with the peptide-Bevacizumab conjugates compared to the Bevacizumab control. Consistent with the binding results in Examples 6 and 7, the peptide-Bevacizumab conjugates with 5 lysines per peptide (Pep-Bevacizumab 1 & 2) were more effective at slowing the delivery rate. In addition, the peptide-Bevacizumab conjugates containing peptides with single flexible spacers showed more sustained delivery rates, consistent with the binding data measured in Example 7.

Figure 11:
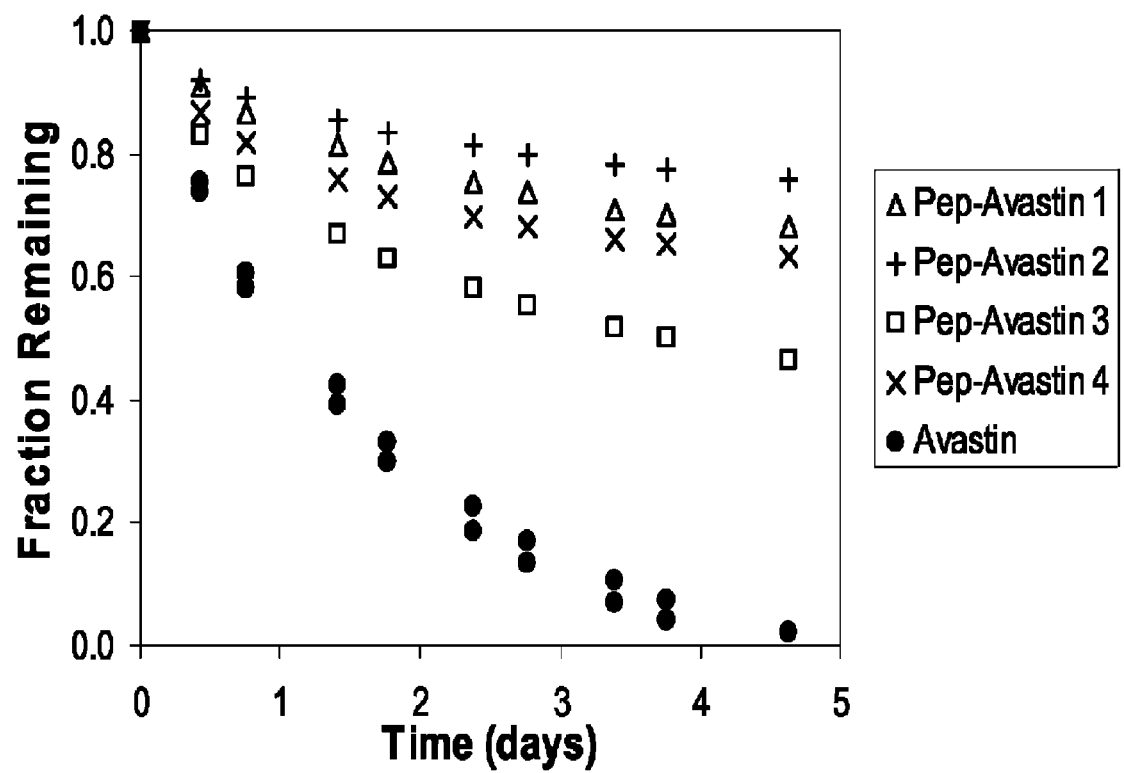
FIG. 11 displays the fraction remaining in the donor as a function of time during the transport study of peptide-Bevacizumab conjugates and non-conjugated Bevacizumab.

FIG. 11 displays the transport data in terms of fraction remaining in the donor as a function of time. Approximately 90% of the Bevacizumab (non-conjugated) loaded is delivered in 3 days, compared to less than half of the peptide-Bevacizumab conjugates.

The release rates for the peptide-Bevacizumab conjugates are relatively constant after the first day for the geometry utilized in this study. Additional in vitro release studies could be performed with volumes and dimensions more similar to in vivo conditions. Furthermore, the composition and number of peptides attached to each therapeutic compound could be optimized to achieve the desired release profile.

This invention is applicable to both large- and small-molecule therapeutics. The therapeutic compounds may be one or more of anti-proliferative agents (e.g., anti-VEGF), hormones, cytokines, growth factors, antibodies, immune modulators, oligos (e.g., RNA duplexes, DNA duplexes, RNAi, aptamers, immunostimulatory or immunoinhibitory oligos, etc.), enzymes, enzyme inhibitors, immune modulators, antimicrobial agents (macrolide antibiotic, micophenolic acid, antifunals, antivirals, etc.), anti-inflammatory agents (e.g., steroids, NSAIDs), etc. The invention is particularly attractive for application to neuroprotective agents and inhibitors of growth factors and angiogenic factors for treatment of degenerative ocular diseases. In addition to Bevacizumab, other therapeutic compounds that bind to and inactivate VEGF include Ranibizumab and VEGF Trap (Regeneron).

In the case of peptides and proteins, modification of therapeutic compounds could be achieved via placement of the peptide "tail" at the C-terminus or N-terminus of the protein using methods such as those established for affinity purification of genetically modified proteins. This invention is particularly relevant to therapeutic compounds that have demonstrated sufficient stability in the vitreous. Ranibizumab, for example, has demonstrated such stability.

The dosage of the intravitreal injections depends upon the required dose of the therapeutic agent and the volume of the formulation. For example, for Ranibizumab, a dosage of 0.5 mg is an effective dosage. This dosage is contained in a formulation volume (e.g., 50 microliters) that is designed to minimize the increase in intraocular pressure during injection.

The current invention advantageously involves minimal excipients and the viscosity of the formulation is low, similar to formulations of an unmodified therapeutic compound. This improves the ability of the dosage to be injected in significantly less time compared to a more viscous solution. The treatment can be administered via an intravitreal injection, enabling widespread use without requiring any additional training or equipment beyond current standard of care. Trauma to the tissue during administration is minimal relative to the surgery required for a non-biodegradable implant and there is no need for invasive procedures to remove a device. Further, the higher doses achievable in the invention contribute to its ability to increase the duration between injections, thereby resulting in fewer injections overall and reduced serious ocular adverse events such as infection and retinal detachment.

Another important advantage of the invention over other biodegradable systems is the molecularly dispersed nature of the therapeutic compound in the in situ-formed depot. Light scattered from microparticles, nanoparticles and liposomes reduces visual clarity, unless an effort is made to match refractive indices. In addition, drug loading in other biodegradable systems can be limited by a combination of light scattering and the need for high levels of excipients to control the delivery rates and achieve stability of the therapeutic compound.

In addition to the vitreous, ocular tissues such as neural retina, sclera, and corneal stroma contain glycosaminoglycans. Hence, in addition to intravitreal injections, in situ depots of the present invention could be formed via injection into other sites such as subretinal space or periocular space (e.g., subconjunctival, sub-Tenon, peribulbar, posterior justrascleral and retrobulbar spaces).

Though the examples noted above describe treatment of the eye, the present invention could also include treatment of tissues other than the eye. Any tissues containing a suitable anionic component (e.g., glycosaminoglycans), may be treated using the methods and cationic compositions described. Other exemplary target tissues include, but are not limited to, brain, skin, cartilage, synovial fluid in joints, as well as some cancers. Alternatively, the biological tissue may contain cationic components, such as bone tissue, and sustained drug delivery could be achieved using the methods and anionic compositions described herein. The compound may be injected locally or systemically, or may be introduced by another means, such as a spraying of droplets while the body is open during surgery. An example is the introduction of an anti-inflammatory agent during a craniotomy to treat subdural hematomas. Similar to the eye, this application benefits from the ability to introduce a sustained source of therapeutic agent with minimal volume expansion, an important feature when trying to minimize edema and intracranial pressure. Hence, the therapeutic compound used in the formulation may vary in both type of drug and indicated use.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A drug composition comprising:
at least one positively charged moiety coupled to a therapeutic compound, wherein the positively charged moiety is a peptide with the amino acid sequence KGSKGSKGSKGSK (SEQ ID NO:1), KGKSKGKSK (SEQ ID NO:2), KGSKGSK (SEQ ID NO:3), or KGKSK (SEQ ID NO:4), and wherein the therapeutic compound is an anti-VEGF compound wherein the spacing of positive charges on the peptide is configured to interact with a spatial arrangement of negative charges on an anionic component to create an in situ depot for prolonged delivery of the anti-VEGF compound.

2. The drug composition of claim 1, comprising a spacer located at a coupling site between the therapeutic compound and the charged moiety.

3. The drug composition of claim 1, wherein the coupling is achieved using a stable covalent bond or a chemically labile covalent bond.

4. The drug composition of claim 1, wherein the anionic component is present in tissue.

5. The drug composition of claim 4, wherein the tissue is eye tissue.

6. The drug composition of claim 5, wherein the eye tissue is vitreous.

7. The drug composition of claim 1, wherein the anionic component is a glycosaminoglycan.

8. The drug composition of claim 7, wherein the glycosaminoglycan is hyaluronic acid.

9. The drug composition of claim 1, wherein the anti-VEGF compound is Bevacizumab.

10. The drug composition of claim 1, wherein the anti-VEGF compound is Ranibizumab.

11. The drug composition of claim 1, wherein the anti-VEGF compound is VEGF Trap.

12. A method of treating the human body comprising:

introducing into a human body a drug composition comprising a charged moiety coupled to a therapeutic compound; wherein the charged moiety is configured to interact with at least one type of component of opposite charge in the human body to create an in situ depot for prolonged drug delivery.

13. The method of claim 12, wherein the drug composition is introduced into the eye.

14. The method of claim 12, wherein the drug composition is introduced into one or more location in the body selected from synovial fluid in a joint, brain, skin, cartilage, or a cancerous region.

* * * * *

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

Lys Gly Ser Lys Gly Ser Lys Gly Ser Lys Gly Ser Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Lys Gly Lys Ser Lys Gly Lys Ser Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Lys Gly Ser Lys Gly Ser Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Lys Gly Lys Ser Lys
1               5
```